United States Patent
O'Donnell et al.

(12) 
(10) Patent No.: US 6,551,468 B1
(45) Date of Patent: Apr. 22, 2003

(54) PREPARATION OF ISOFLURANE BY REACTION OF 2,2,2-TRIFLUOROETHYL DIFLUORO-METHYL ETHER AND CHLORINE IN ADDED WATER, AT LOW TEMPERATURES AND/OR AT HIGHER CONVERSIONS

(76) Inventors: William J. O'Donnell, 1 Seventh St. Unit 1202, Augusta, GA (US) 30904; Paul Mazzell, Jr., 127 Travellers La., Aiken, SC (US) 29803; Lee G. Sprague, 1316 Buena Vista Rd., Augusta, GA (US) 30909; Arthur J. Elliott, P.O. Box 1302, Sonoita, AZ (US) 85637

( * ) Notice: Subject to any disclaimer, the term of this patent is extended or adjusted under 35 U.S.C. 154(b) by 0 days.

(21) Appl. No.: 09/529,202
(22) PCT Filed: Oct. 15, 1998
(86) PCT No.: PCT/US98/21997
§ 371 (c)(1),
(2), (4) Date: Aug. 21, 2000
(87) PCT Pub. No.: WO99/20588
PCT Pub. Date: Apr. 29, 1999

Related U.S. Application Data
(60) Provisional application No. 60/062,284, filed on Oct. 17, 1997.

(51) Int. Cl.$^7$ ................................................. C07C 45/00
(52) U.S. Cl. .................................................. 204/157.92
(58) Field of Search ..................................... 204/157.92

(56) References Cited

U.S. PATENT DOCUMENTS
5,416,244 A * 5/1995 Rozov et al. ................ 568/684

OTHER PUBLICATIONS
Reference A was cited on International Search Report.*

* cited by examiner

*Primary Examiner*—Edna Wong
(74) *Attorney, Agent, or Firm*—Norris McLaughlin & Marcus

(57) ABSTRACT

A process for preparing isoflurane (1-chloro-2,2,2-trifluoroethyl difluoromethyl ether) by reacting PFE (2,2,2-trifluoroethyl difluoromethyl ether) with chlorine in the presence of ultraviolet light and added water, at a low temperature and/or at a high conversion.

13 Claims, No Drawings

PREPARATION OF ISOFLURANE BY REACTION OF 2,2,2-TRIFLUOROETHYL DIFLUORO-METHYL ETHER AND CHLORINE IN ADDED WATER, AT LOW TEMPERATURES AND/OR AT HIGHER CONVERSIONS

This application is a 371 of PCT/US98/21997, filed Oct. 15, 1998, which is, in turn, claims benefit to U.S. Provisional Application No. 60/062,284, filed on Oct. 17, 1997, priority of which is hereby claimed under 35 U.S.C. §120.

BACKGROUND OF THE INVENTION

1. Field of the Invention

The present invention relates to an improved process for preparing isoflurane from PFE.

2. Description of Related Art

The compound isoflurane (1-chloro-2,2,2-trifluoroethyl difluoromethyl ether) has the structural formula:

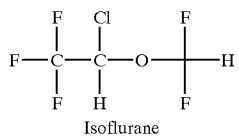
Isoflurane and is a well known anesthetic. The compound, and methods for its preparation are described in U.S. Pat. Nos. 3,535,388, and 3,535,425. Its pharmacological properties are described in *Anesthesiology* 35, 8–53 (1971); and in *Can. Anaesth. Soc. J.* 18, 376–407 (1971).

The conventional process for preparing isoflurane involves reaction of 2,2,2-trifluoroethyl difluoromethyl ether, (or "pentafluoro ether" which is also known as "PFE"), and has the structural formula:

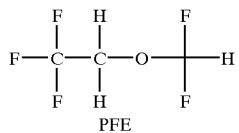
PFE with elemental chlorine under light. Thus, the chlorination reaction proceeds according to the following scheme:

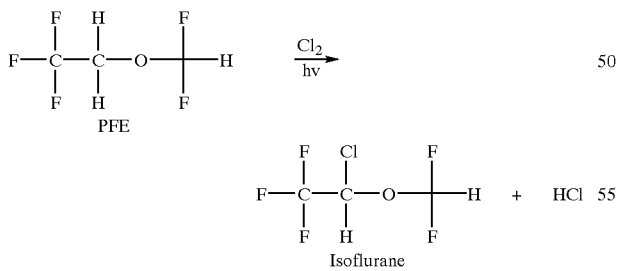

In the conventional process, the chlorine is introduced into a vessel containing substantially dry PFE illuminated with an ultraviolet light in a quartz housing. This process requires an expensive vessel made of corrosion-resistant alloy capable of withstanding HCl under pressure. In fact, during the chlorination reaction the pressure continues to increase because of the continuing production of HCl. To mitigate this problem it is necessary to remove HCl during the process without losing chlorine, PFE or the product. This requires a high pressure, corrosion-resistant alloy fractional distillation column with a low temperature condenser to provide the refluxing of liquid HCl necessary to separate the components of the mixture. Even with this elaborate distillation procedure there are losses of reactants with the removed HCl. Moreover, several impurities are generated, which are difficult to separate from the isoflurane product.

Accordingly, there is the need in the art for an improved process for preparing isoflurane, which removes the need for elaborate distillation procedures, corrosion-resistant pressure vessels, and elaborate drying procedures, and eliminates the losses encountered with the removed HCl, and reduces the amounts of impurities generated.

SUMMARY OF THE INVENTION

These and other objects were met by the present invention, which relates to an improved process for preparing isoflurane, which comprises reacting 2,2,2-trifluoroethyl difluoromethyl ether with chlorine in the presence of light, wherein the improvements comprise conducting the reaction in the presence of water, choosing the temperature to improve the yield, and using higher conversions to lower costs with little effect upon yield.

DETAILED DESCRIPTION OF THE INVENTION

The conventional process is essentially a "dry" process requiring a reduction in the amount of water present in the reaction vessel to very low levels, i.e., less than about 50 parts per million of the total weight of the reactants. According to a first embodiment of the present invention, water is added deliberately. In a preferred embodiment, there should be sufficient water present to dissolve all of the hydrogen chloride generated in the reaction. The amount of water, of course, will increase as the desired conversion of the reactants is increased. An example is that at least 13% of the mixture should be water for a conversion of 50% at 0° C. More water is not harmful and lesser amounts of water will still be beneficial but the pressure of the undissolved hydrogen chloride would have to be allowed for in the equipment. In a preferred embodiment, the amount of water should be a minimum of about 4%, again based on the total weight of the reactants. In the particularly preferred embodiment, the amount of water should be at least 13% based on the total weight of the reactants.

It has been found that the deliberate addition of sufficient water to the reaction mixture also removes the requirement of a pressure vessel and the continuous removal of HCl with its attendant column and refrigeration.

Thus, according to the present invention, the chlorination reaction can be performed in a low pressure, glass-lined vessel sealed off from the atmosphere at pressures as low as the vapor pressure of the reactants to slightly above atmospheric pressure. Chlorine is added as done in the conventional process but no pressure is produced because the HCl dissolves in the aqueous layer.

The temperature of the reaction can be varied over a wide range, but, according to a second embodiment of the present invention, preferably is in the range of −15 to +30° C.

When the desired conversion is reached, the layers are separated and the organic layer is washed with base such as sodium hydroxide and then is further purified by distillation. The unreacted PFE is readily recycled for further chlorination.

An ultraviolet lamp is the preferred source of light but any light capable of dissociating chlorine into atoms may be used. This includes light in the visible region. Depending on the size of the reactor, commercially available wattages of ultraviolet lamps can be used. These are available from Hanovia and others.

The reaction may be performed either by batch or continuous methods depending on typical engineering choices.

During the conventional chlorination process there are several significant by-products formed. These are products of competing chlorination reactions which are not affected by the inventive "wet" conditions or the convention al "dry" conditions. However, under the conditions of the "dry" high pressure reaction, several minor organic impurities are also generated, some of which are difficult to separate from the product. Thus, for example, Table 1, run 2 shows the formation of 2,2,2-trifluoroethyl chlorofluoromethyl ether, E-244 and 2,2,2-trifluoroethyl dichloromethyl ether, E-243. In comparable "wet" runs 3–6 these are essentially eliminated. Also, in the "dry" process the diethyl ethers, 1-chloro-2,2,2-trifluoroethyl 2',2',2'-trifluoroethyl ether, E-346 and 1,2,2,2-tetrafluoroethyl 2',2',2'-trifluoroethyl ether, E-347 are made at low levels [runs 1 and 2], but because of close boiling points they are difficult to remove from isoflurane by distillation. In the "wet" process these ethers are virtually eliminated [runs 3–6]. Finally, the category called "Unknowns" in Table 1 is reduced by wet conditions.

It can also be seen that in the "dry" process, a substantial amount of fluoride ion is made [see Table 1, runs 1 and 2]. The fluoride ion attacks the quartz housing required for the transmission of ultraviolet light from a lamp to the reaction mixture. Fluoride ion is minimized under the "wet" process [runs 5 and 6].

the desired product, isoflurane, increases in the reaction mixture and it becomes a reactant with chlorine. Table 2 below shows only a small decrease in yield even after the reaction mixture contains more isoflurane than PFE. Thus, higher conversions can be used without dramatically affecting the yield of the desired isoflurane product. Accordingly, a third embodiment of the present invention involves conducting the reaction over a conversion range of about 10 to 70%, preferably about 20 to about 60%, more preferably about 30 to about 50%.

TABLE 2

| Conversion, % | 10 | 20.1 | 34 | 40.1 | 50.1 | 60.5 | 70 |
|---|---|---|---|---|---|---|---|
| PFE | 90.0 | 80.2 | 67.0 | 61.7 | 52.7 | 43.5 | 38.7 |
| ISF | 9.4 | 18.6 | 30.5 | 35.3 | 42.9 | 50.3 | 54.1 |
| Isomer | 0.5 | 0.9 | 1.6 | 1.8 | 2.1 | 2.5 | 2.5 |
| GEM | 0.1 | 0.3 | 0.8 | 1.7 | 2.0 | 3.2 | 4.3 |
| Dichlor | <0.01 | 0.04 | 0.1 | 0.1 | 0.3 | 0.5 | 0.3 |
| ISF Yield*, % | 94.0 | 94.0 | 92.4 | 92.2 | 90.7 | 89.0 | 88.4 |

*Yield calculation: 100 × % of ISF/total % of products
PFE = 2,2,2-Trifluoroethyl difluoromethyl ether
ISF = 1-Chloro-2,2,2-trifluoroethyl difluoromethyl ether
Isomer = 2,2,2,-Trifluoroethyl chlorodifluoromethyl ether
GEM = 1,1-Dichloro-2,2,2-trifluoro difluoromethyl ether
Dichlor = 1-Chloro-2,2,2-trifluoroethyl chlorodifluoromethyl ether It has discovered that the relative yields of isoflurane and its isomer, 2,2,2-trifluoroethyl chlorodifluoromethyl ether, depends markedly on the temperature of thee chlorination reaction. Table 3 below shows the ratio of yields of the isoflurane to its isomer increases dramatically as the temperature is lowered from 60° C. to −45° C. Thus, the reaction

TABLE 1

| Run # | Reference | Process | Temp (° C.) | Press (Psia) | H$_2$O (%) | F-ion (ppm) | E-347 [b] (ppm) | E-244 [c] (ppm) | E-346 [d] (ppm) | E243 [e] (ppm) | Unknowns (ppm) |
|---|---|---|---|---|---|---|---|---|---|---|---|
| 1 | J19501 [a] | dry | 22 | 115 | <0.0010 | 240 [f] | [g] | — | — | — | 6600 |
| 2 | 122-01-03 | dry | ~30 | 20–52 | <0.0010 | 185 | [g] | 9968 | 61 | 2793 | — |
| 3 | 124-31 | wet | 5–15 | ~15 | 4.2 | — | <2 | <2 | <2 | <2 | — |
| 4 | 124-35 | wet | ~30 | ~15 | 4.2 | 22 | <2 | 3 | <2 | <2 | — |
| 5 | J19705A1 [h] | wet | 2.4–12 | 16–23 | 19.3 | 18 | — | <2 | — | 2 | 200 |
| 6 | J19705C1 | wet | 22–38 | 16–24 | 19.3 | <10 | <2 | — | — | — | 100 |

[a] Reference, 21795/0105
[b] E-347 = 1,2,2,-Tetrafluoroethyl 2',2',2'-trifluoroethyl ether
[c] E-244 = 2,2,2-Trifluoroethyl chlorofluoromethyl ether
[d] E-346 = 1-Chloro-2,2,2-trifluoroethyl 2',2',2'-trifluoroethyl ether
[e] E-243 = 2,2,2-Trifluoroethyl dichloromethyl ether
[f] Steady state value while removing F ion by circulating mixture over SiO$_2$ gel bed
[g] At various times the crude isoflurane contains > 100 ppm
[h] Recycled PFE, 97%

In addition to these problems of the "dry" process, in order to meet the rigorous specifications of the pharmaceutical product another difficult fractional distillation must be performed to remove traces of acidity from isoflurane. This has to be done while trying to prevent new adds from forming by decomposition during that process.

The inventive "wet" process tolerates up to 10% of organic impurities in the reactant PFE as well [see Table 1, run 5]. It has the further advantage of leaving the recovered PFE in a purer state. Also, the loss of reactants with the removed HCl is eliminated.

Surprisingly, the level of conversion of PFE to isoflurane may be varied considerably because the yield of product diminishes only slightly as the conversion rises from 10% to 70%. Normally, the level of overchlorinated product would be expected to increase significantly as the concentration of should be run at the lowest temperature allowed by practically and economy.

TABLE 3

| Temperature (° C.) | Yield Ratio (Isoflurane %/Isomer %) |
|---|---|
| 60 | 11 |
| 30 | 14.5 |
| 5 | 21 |
| −45 | 46 |

It will be appreciated that the instant specification and claims are set forth by way of illustration and not limitation, and that various modifications and changes may be made without departing from the spirit and scope of the present invention.

What is claimed is:

1. A process for preparing 1-chloro-2,2,2-trifluoroethyl difluoromethyl ether comprising reacting 2,2,2-trifluoroethyl difluoromethyl ether with chlorine in the presence of light in the presence of added water.

2. The process according to claim 1, wherein the light is ultraviolet light.

3. The process according to claim 1, wherein the added water is an amount of water which is sufficient to dissolve all of the hydrogen chloride generated by the reaction.

4. The process according to claim 1, wherein the added water is at least 4% by weight of water, based on the total weight of the reactants.

5. The process according to claim 1, wherein the reacting is conducted at a temperature of from about −15 to about +30° C.

6. A process for preparing 1-chloro-2,2,2-trifluoroethyl difluoromethyl ether comprising reacting 2,2,2-tifluoroethyl difluoromethyl ether with chlorine in the presence of light over a conversion range of about 10 to about 70%.

7. The process according to claim 6, wherein the reacting is conducted in a substantially dry state.

8. The process according to claim 6, wherein the reacting is conducted in the presence of an amount of water which is sufficient to dissolve all of the hydrogen chloride generated by the reaction.

9. The process according to claim 6, wherein the light is ultraviolet light.

10. The process according to claim 6, wherein the reacting is conducted in the presence of at least 4% by weight of water, based on the total weight of the reactants.

11. The process according to claim 6, wherein the reacting is conducted at a temperature of from about −15 to about +30° C.

12. The process according to claim 6 for preparing 1-chloro-2,2,2-trifluoroethyl difluoromethyl ether comprising reacting 2,2,2-tifluoroethyl difluoromethyl ether with chlorine in the presence of light over a conversion range of about 20 to about 60%.

13. The process according to claim 6 for preparing 1-chloro-2,2,2-trifluoroethyl difluoromethyl ether comprising reacting 2,2,2-trifluoroethyl difluoromethyl ether with chlorine in the presence of light over a conversion range of about 30 to about 50%.

* * * * *

UNITED STATES PATENT AND TRADEMARK OFFICE
CERTIFICATE OF CORRECTION

PATENT NO. : 6,551,468 B1
DATED : April 22, 2003
INVENTOR(S) : O'Donnell et al.

It is certified that error appears in the above-identified patent and that said Letters Patent is hereby corrected as shown below:

Column 5,
Line 18, "tifluoroethyl" should read -- trifluoroethyl --

Column 6,
Line 13, "tifluoroethyl" should read -- trifluoroethyl --

Signed and Sealed this

Seventeenth Day of August, 2004

JON W. DUDAS
*Acting Director of the United States Patent and Trademark Office*